United States Patent [19]
Sottery

[11] Patent Number: 6,023,661
[45] Date of Patent: Feb. 8, 2000

[54] STREAMING POTENTIAL SYSTEM AND METHOD

[75] Inventor: John P. Sottery, Milford, Conn.

[73] Assignee: Bristol-Myers Squibb Company, New York, N.Y.

[21] Appl. No.: 08/733,847

[22] Filed: Oct. 18, 1996

[51] Int. Cl.[7] .................................................. C25B 11/00
[52] U.S. Cl. ........................... 702/45; 204/232; 204/242
[58] Field of Search ............................. 364/499; 429/90, 429/122; 204/232, 242, 253, 254, 280, 293.03

[56] References Cited

U.S. PATENT DOCUMENTS 4,427,944   1/1984   Chandler .................................. 324/353

Primary Examiner—Emanuel T. Voeltz
Assistant Examiner—Thomas Peeso
Attorney, Agent, or Firm—Morton S. Simon

[57] ABSTRACT

A fully automated computer controlled system and method to simultaneously measure in a dynamic mode the streaming potential, impedance and permeability resulting from a flow of various liquids through a sample, particularly a compressed mass of human hair. The system includes four air-pressurized reservoirs and three test cells, each test cell containing a sample to be tested. An impedance measurement is made by impressing a signal wave train across each sample over a selected range of frequencies, preferably in the 10–10,000 Hz range, rather than at a single frequency. The air pressure is controlled within 2% of a selected pressure and the outlet flow of liquid from the test cells is continually measured to provide an accurate and reproducible set of measurements.

18 Claims, 3 Drawing Sheets

STREAMING POTENTIAL SYSTEM AND METHOD

FIELD OF THE INVENTION

The present invention relates to scientific measurement systems and methods and more particularly to a system and method for the simultaneous determination of dynamic streaming potential, dynamic conductivity, dynamic permeability, dynamic zeta potential, dynamic refractive index, dynamic color and the analysis of the sorption and desorption of ions on porous or non-porous material, such as a hair sample, through which a liquid is flowed.

RELATED ART

The measurement of streaming potential involves flowing an electrolytic solution through a permeable body, for example, a plug of hair. The flow of liquid through the permeable body produces an electrokinetic force (current or potential), called the streaming potential, which may be measured by an electrometer.

The streaming potential may be used to evaluate zeta potentials at solid-liquid interfaces. The zeta potential $\zeta$ may be simply defined (without corrections) as follows:

$$\zeta = \frac{4\pi nkE}{PD}$$

where E is the streaming potential, n is the viscosity of the liquid, k is the conductivity of the liquid, P is the applied pressure on the liquid, and D is the dielectric constant of the liquid.

If the pressure is constant and the same liquid is used for a series of experiments, the zeta potential for that series of experiments is directly proportional to the streaming potential, i.e., the only variable is the streaming potential.

Generally, apparatus to measure the streaming potential uses a plug of porous or non-porous material, for example, glass fibers, clay and other mineral particles, held between perforated electrode plates. Liquid is forced through the plug, by compressed air, or pulseless pump, from a liquid supply reservoir to a collection reservoir.

The electrical potential E (streaming potential measured in volts) is measured by an electrometer connected to the two electrodes. The streaming potential depends upon the presence of an electrical "double layer" at a solid-liquid surface, i.e., the surface of the hairs of the plug and the liquid flowing through the hair plug. The electrical double layer consists of ions of one charge type, i.e., positive, fixed to the surface of the solid and an equal number of mobile ions of the opposite charge, i.e., negative, distributed through the neighboring region of the liquid. The liquid moving over the solid surface causes an electric current, because its flow displaces the mobile ions with respect to the fixed charges on the solid surface. The potential which would be required to reduce that net flow of electricity to zero is the streaming potential.

An "Electro-Kinetic Analyzer" which may measure streaming potential and streaming current on a plug of fibers using silver/silver chloride electrode disks is available as the "Paar-K1-EKA" from Brookhaven Instruments, Holtsville, N.Y. However, that system, and others commercially available, measure the sample in a static mode. The sample is manually loaded, unloaded and reloaded at each step of the test. Such systems may produce streaming potential measurements which are not stable, i.e., the data is scattered for the same material and the same conditions. Such lack of stable and reproducible results may arise because the pads (or plugs) are made non-uniformly, air bubbles are entrapped in the pad (or plug), and/or the electrodes become polarized. However, even with care, the results may not be reproducible since the streaming potential, conductivity and permeability are often time-dependent. They can change, for example, during the rinsing of the fibers with a test solution, because of surface hydration, rearrangement of surface layers, and desorption of surfactants, lipids, polymers, etc.

U.S. Pat. No. 5,452,233 entitled "Streaming Potential System And Method" is assigned to Clairol, Inc., the assignee of the present application, and is incorporated by reference herein. In that patent, streaming potential, conductivity and permeability of a single porous hair sample are measured by flowing, in sequence, a test solution and treatment solution through the sample held in a test cell. The solutions are flowed from reservoir bottles which are under air pressure. Although the air pressure is monitored by a pressure gauge, changes in air pressure of even 2% may result in uneven data and there is no provision for an exact (within 1%) selection of an air pressure. The flow rate is measured gravimetricly using an electronic balance, whose results are delayed, for example, by 30 seconds, for each measurement of flow. That system was not designed to measure impedance (conductivity) effects over a range of frequencies. That system does not discriminate between solution conductivity and a surface conductivity of the substrate (sample). It is designed to provide one measurement of the combined solution and surface conductivity. However, in practice it is important to differentiate between the surface conductivity and liquid conductivity, especially in situations when the dynamics of a change in the ionic moieties leaching out from the substrate (sample) should be monitored, for example, in the case of bleached or waved hair.

A proper value of solution conductivity must be used for calculation of zeta potential. Otherwise, the zeta potential does not provide a true meaning.

Additionally, the system of U.S. Pat. No. 5,452,233 does not measure conductivity of the sample during a treatment application. Also, the electrometer system of that patent is too slow to measure double-layer relaxation effects. Furthermore, it does not measure the conductivity of the liquid before it flows into the test cell and as it exits the test cell. Also, it does not allow for an adjustment of the duration of the "on" and "off" flow cycles. This feature is important in an assessment of electrode polarization characteristic at a particular flow cycle setting and consequently this information would allow for a considerable time savings during the tests, especially in the multiple treatment evaluation modes.

SUMMARY OF THE INVENTION

In accordance with the present invention there is provided a method and system for measuring electrokinetic parameters in a dynamic fashion, namely streaming potential, zeta potential and conductivity (over a range of frequencies), as well as refractive index, permeability (flow rate) and color. The following description uses a plug of human hair fibers as its embodiment of a test sample. However, the system and method may be used for measuring other samples, such as other fibers, porous materials, and non-porous materials such as glass fibers and clays which may be formed into a sample plug through which liquid may be flowed.

The system comprises a series of reservoirs (liquid containers), for example a test solution reservoir, to provide the initial (baseline) values, and first, second and third liquid treatment reservoirs. Compressed air, or a pulseless air pump, is connected through a computer-controlled precision pressure regulator to the reservoirs to maintain a constant pressure on the liquids. The reservoirs are connected, by fluid flow lines, through a matrix of solenoid valves, through a conductivity cell and then to the inlet orifice of one of three test cells. The inlet orifices of the test cells are connected to a pressure transducer which measures liquid pressure at each orifice. The outlet orifices of the test cells are connected, via a matrix of solenoid valves, to a flow line which has, in series, a conductivity cell, a pressure transducer, a flow meter, a refractive index meter, a color meter and a drain.

Each test cell (flow cell) has perforated electrode disks at its opposite ends. A hair plug is held between the electrode disks in a liquid-tight insulative housing. Each pair of electrode disks is connected, via shielded coaxial cables, to a high performance, low-noise matrix switch (employing mercury wetted contacts). This matrix switch, under computer control, connects each test cell (containing a pair of electrodes), one cell at a time, either to an electrometer or to a multi-frequency impedance analyzer.

The liquid pressure transducers, electrometer, conductivity meters, impedance analyzer, flow meter, refractive index meter, air pressure regulator, color meter and valves are connected to a PC (Personal Computer) through an I/O (Input/Output) circuit board. The I/O board is a high performance I/O board utilizing a set of A/D (Analog/Digital) converters and a set of D/A (Digital/Analog) converters. The computer, under software (program) control, operates the valves, collects and displays the data from the various instruments and transducers.

In operation, the user will load one, two or three test cells with hair samples, for example, normal, damaged, and pre-washed hair samples. A hair sample may be a plug of untreated and cleaned brown Caucasian human hair. The system, in a dynamic mode, will measure the streaming potential, impedance and permeability of each sample, in sequence. The system will automatically flow, in a unidirectional stream, a dilute test solution of a salt through the first test cell. Alternatively, the system may flow the solutions both forward and reverse (backwards) through the test cells. The flow, conductivity, potential and refractive index are measured to provide a baseline (untreated) signal. One treatment solution is then flowed through the first test cell to provide an on-line treatment of that hair sample. The streaming potential, impedance, refractive index and permeability of the hair sample are again measured. The same hair sample may be retreated, on-line, with the same treatment solution or with a second treatment solution or a third treatment solution by applying flows of the liquids through the hair sample. Then the test solution is again flowed through the first test cell, and data is recorded. This same procedure can then be followed for the samples in the second and third test cells, for example, plugs of chemically fixed hair, i.e., bleached or waved hair. The entire procedure is computer-controlled and without operator intervention. Preferably the tests for the first sample are completed, then the second sample is tested and then the third sample is tested. Alternatively, the three samples are tested simultaneously and their electrodes are energized and then sampled by a high-speed multiplex system. The durations of the "on" and "off" flow cycles are controlled by the computer and may be adjusted, under operator control, depending on test requirements.

The system of the present invention permits simultaneous measurement of liquid conductivity of effluent from the hair plug (sample) in the dynamic mode. This information is especially important when a high conductivity value is observed for chemically treated hair and its origin cannot be easily ascribed to surface or liquid conductivity.

Another improvement of the system is that it permits an easily obtained calculation of the swellability of a test material (for swellable media). Two pressure transducers measure the liquid pressure directly before and after the test cell. This arrangement provides data to calculate pressure drop due to the filling of the plug (sample), e.g., the swelling of the plug. Using the Kozney-Carman equation one may calculate the volume of a filling material, based on the measured values of applied pressure, plug density and pressure drop due to the bed material.

BRIEF DESCRIPTION OF THE DRAWINGS

The following detailed description, taken in conjunction with the accompanying drawings, provides the inventor's presently known best mode of practicing the invention.

In the drawings.

DETAILED DESCRIPTION OF THE INVENTION

Figure 1:
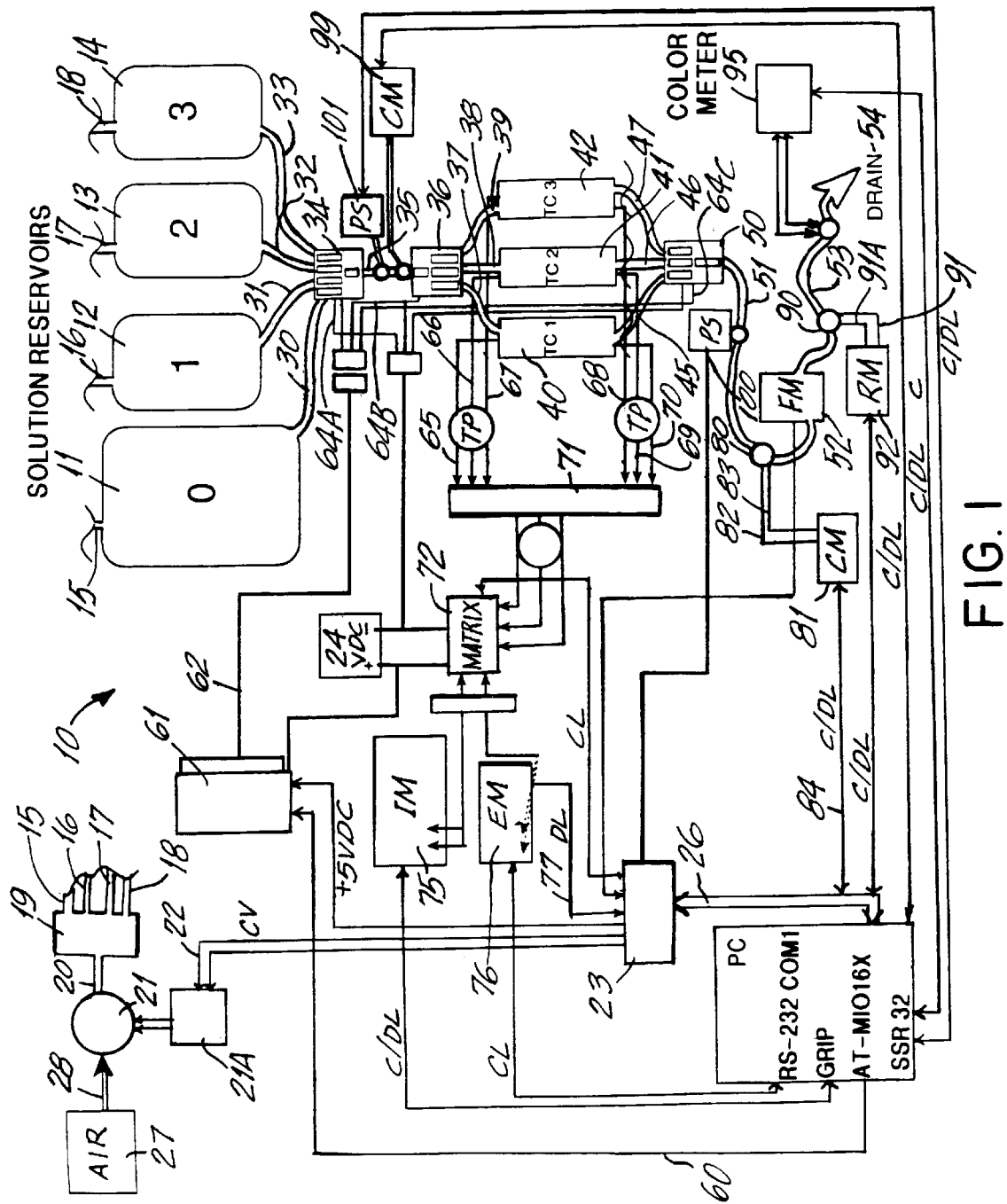
FIG. 1 is a block diagram of the system of the present invention.
Figure 2:
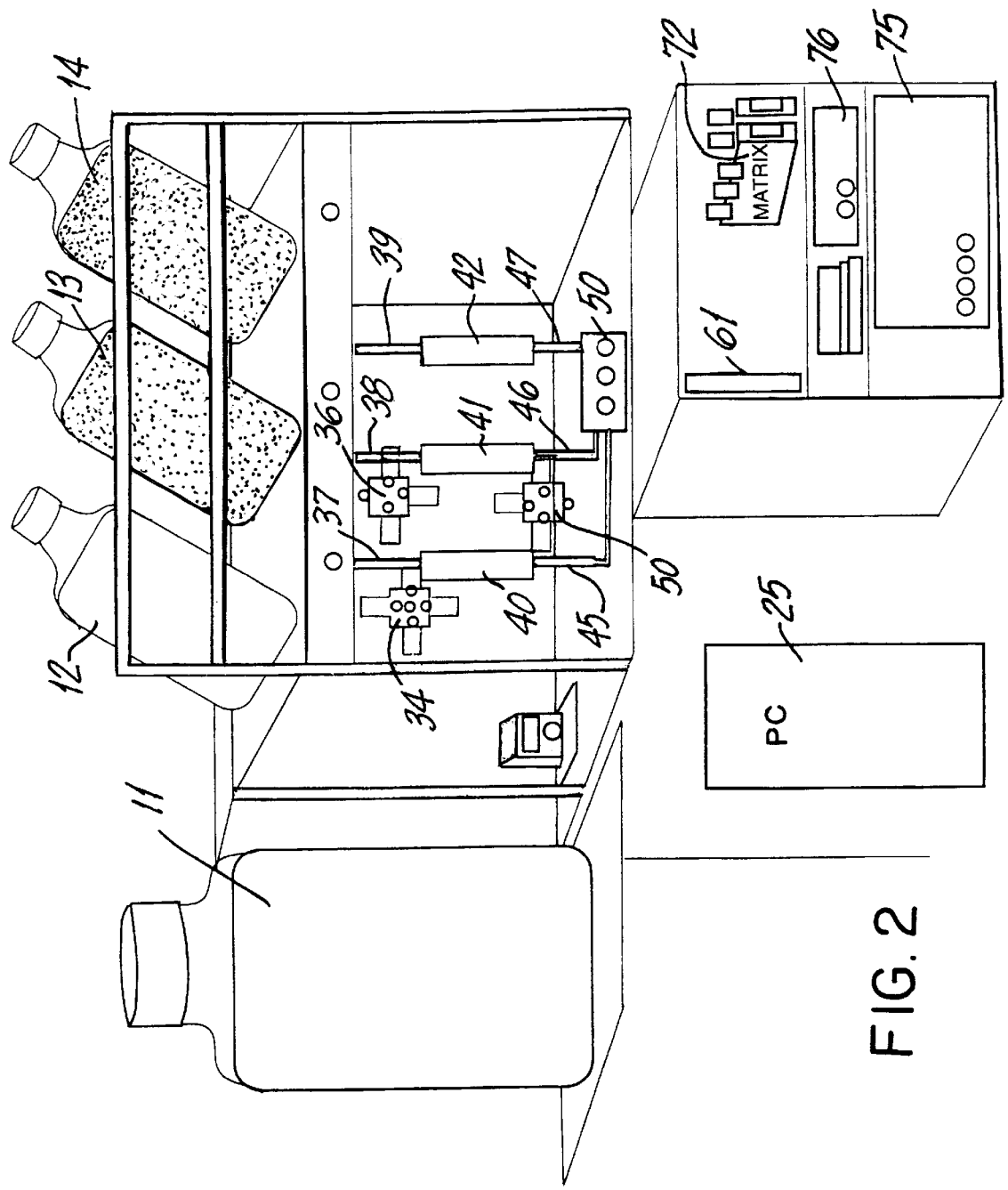
FIG. 2 is a diagram of a portion of the system of the present invention showing the positions of some of its components.
Figure 3:
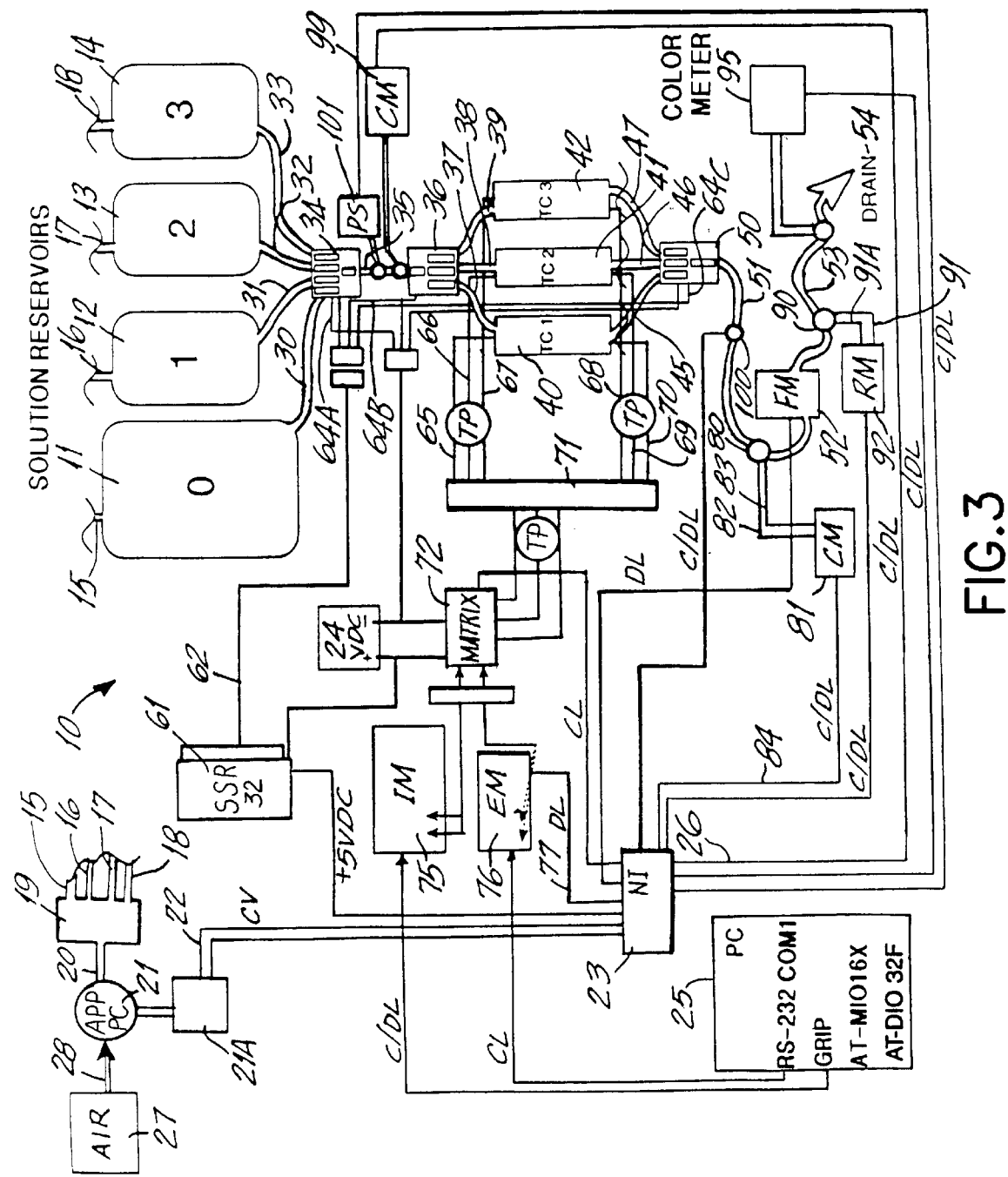
FIG. 3 is a block diagram similar to FIG. 1.

As shown in FIG. 1, the system 10 includes four reservoirs 11–14' (labeled 0–3). A large reservoir 11 contains the standard liquid test solution which provides a baseline standard for the measurements. Preferably the liquid in reservoir 11 is an aqueous solution of KCl at a concentration of $5 \times 10^{-5}$M in ultra-pure deionized water (less than 3 parts per million of contamination). The reservoirs 12–14 contain the treatment liquids which are to be measured, typically hair shampoos, hair surfactants, hair conditioners, hair dyes, hair polymers and hair active treatments such as oxidizing or reducing solutions. Specific non-limiting examples of such treatment liquids are described in the above-mentioned U.S. Pat. No. 5,452,233.

A uniform and selectable air pressure is applied to the reservoirs 11–14 through air lines 15–18 leading from air manifold 19 having inlet air line 20. The inlet air line 20 is connected to a precision regulator 21 (valve) whose pressure setting is controlled, by regulator control unit 21A, which in turn is connected via control voltage lines 22, to electronic I/O (Input/Output) board 23, Model CV-50, available from National Instruments, Austin, Tex. 78730-5039. The board 23 includes a set, for example eight, of D/A (Digital/Analog) converters and a set, for example 8, of A/D (Analog/Digital) converters. The I/O board 23 generates analog command signals based upon digital data generated by a suitable PC 25 (Personal Computer), preferably a Hewlett-Packard™ which communicates to board 23 over communication line 26. The preferred software platform is "LabView"™, available from National Instruments.

As used on the drawings, the letters PC means personal computer, DL means data line, CL means communication line, TP means test point, PS means pressure sensor, CV means control voltage (analog voltages), CM means conductivity measurement, EM means potential measurement, FM means flow measurement, IM means impedance measurement and GPIB means General Purpose Interface Bus.

A source of air pressure 27 is connected through air line 28 to the input of high performance head pressure regulator 21. A suitable regulator valve is Model CVC-1PA, available from Advanced Pressure Products, Ithaca, N.Y. 14850-1298 which uses a needle valve and a diaphragm and which is driven by a step motor. The PC 25 generates digital control data which are converted to analog control voltages by the D/A converter of input/output board 23. These analog control voltages are then transmitted to the regulator control unit 21A, which in turn converts those control voltages into pulses to operate the step motor of regulator 21. Preferably the air pressure is set at 2.5 pounds per square inch (over atmospheric pressure), by the control computer PC 25, and is held at the selected pressure preferably within 2% and most preferably within 1% i.e. ±0.025 lbs./sq.in. This exact and selectable pressure, without air surges, is important. If the pressure varies from test to test, or within a test, the flow, and the measurements relating to flow, will also vary in an uncontrolled manner, leading to inaccuracies of the measurements.

The reservoirs 11–14 are connected to fluid outlet tubes 30–33, respectively. The tubes 30–33 are connected to valve matrix 34 (four inlet—one outlet) which is designed to permit flow from any one reservoir to its outlet tube 35. This valve matrix, and the other valve matrices, use highly inert solenoid-operated liquid open/closed valves. The tube 35 is connected as the inlet to pressure sensor (pressure transducer) 101 and then to a first conductivity cell 99A, which in turn is connected to conductivity meter 99, both discussed below, and then to a second valve matrix 36 (one-inlet—three outlet) which is designed to flow liquid to any one of three outlet liquid flow tubes 37–39, either in sequence or to any two of the outlet tubes 37–39 or to all three outlet tubes 37–39 simultaneously.

A conductivity measurement is made of the liquid flowing in tube 35 by the conductivity meter (CM) 99. The liquid flows through a cell having a pair of porous electrode disks set at a fixed spacing in an insulative housing. The electrodes are electrically connected to a conductivity meter 99 which produces an output which it communicates to PC 25.

An alternative, not shown in FIG. 1, is to connect the electrodes of the flow-through cells, used to measure conductivity, to a low impedance switching matrix. The electrodes may then be connected, one pair at a time, using a multiplexing control of the switch matrix, to the impedance analyzer 75. This would avoid the use of the separate conductivity meters 81 and 99. The pressure of the liquid flowing in tube 35 is measured by pressure sensor 101. A suitable pressure sensor (pressure transducer) is available from SETRA (Acton, Mass. 01720).

The tubes 37–39 are connected at the inlet orifices of test cells 40–42, respectively (TC1, TC2, TC3). Each of the test cells 40–42 (flow cells) has a top porous electrode and a bottom porous electrode, the electrodes preferably being silver/silver chloride screen disks. The electrodes are held in a leak-proof insulative housing. Liquid flows, preferably one test cell at a time, from an inlet tube 37–39 through the two porous electrodes and out the respective outlet tube 45–47. A sample, for example, a hair sample (hair plug), is held in a test cell and positioned between the electrodes. Preferably each hair sample is packed into its test cell so that the hair is partially compressed; but not so compressed as to block the flow of liquid at the preferred applied pressure.

The three test cells permit the testing of three different hair samples using the same conditions, including the same liquids, air pressure and room temperature. For example, the hair sample in test cell 40 is normal hair, the hair sample in test cell 41 is dry hair, and the hair sample in test cell 42 is damaged hair. As another example, the hair sample in test cell 42 is dark normal hair and the hair sample in test cell 42 is the same lot of hair after treatment with a dye.

The outlet tubes 45–47 are connected to a third valve matrix 50 (three-inlet one-outlet) whose outlet tube 51 is connected to a precision flow meter 52. The flow meter drains through outlet tube 53 to the drain 54. A suitable flow meter is Model 111 available from McMillan Company, Georgetown, Tex. 78627-1340. The flow meter 52 provides continuous digital output of flow, i.e., every $1/10$ second, of the volume of flow of the liquid. In contrast, an "analytical beaker" (a beaker which is automatically weighted) would provide flow measurements for example, only every 30 seconds and with a 30-second delay and would involve emptying of the beaker during the runs.

The complete system 10 is automatically controlled by the programmed PC 25. The PC 25 sends digital control signals over line 60 to the controller board 61 located on a mounting rack which via optical isolators (optically isolated relays), converts the digital control signals to fixed analog control voltages, preferably at 24 volts d.c. (direct current). The optical relays isolate the computer system from potentially damaging voltages arising from the system. In addition, the optical relays isolate the test cells from the computer system noise and eliminate potential ground loops and their corruption of the signal. This design yields a significant improvement in the signal-to-noise ratio of the measurements. A suitable controller board is Model PB32D with SSR32/ODC5 output modules from Gordos Arkansas, Inc., the board being available from National Instruments, Austin, Tex. 78730–5039. The output analog control signals from board 61 are communicated over multi-line cable 62, which is a cable having 12 lines. The outputs over lines 64A–64C are to the first, second and third valve matrices, respectively, namely, matrix 34, matrix 36 and matrix 50. For example, the line 64A is a cable having five lines, one line connected to each valve of the valve matrix 34.

Alternatively, digital valves may be used in which each valve in each valve matrix is coded and a valve setting is associated with the code. Each valve is activated by its code and is set by the digital command.

Each test cell 40–42 has a pair of electrodes consisting of a top and a bottom electrode. The top electrodes are connected to electrical lines 65–67 and the bottom electrodes are connected to electrical lines 68–70, respectively. The lines 65–70 are connected to a computer controlled electrical switching matrix 71 (6 lines in–2 lines out) which uses mercury wetted switches. Such high performance switches present an extremely low impedance over the relevant range of frequencies, i.e., the switches are transparent to the signals. A suitable matrix is Model 7803-TTL-24V twinaxial relay module available from Matrix Systems Corp., Calabasas, Calif., which presents a selectable switch which is essentially noise-free and transparent to the signals over the frequency range of 10 Hz to 10,000 Hz. The matrix 71 is connected by lines to the same type of low noise switching matrix 72.

The matrix 72 is connected to impedance measurement analyzer 75 (IM), preferably a digital output multi-frequency Model 4192A LF from Hewlett-Packard Co., Paramus, N.J. 07652.

The matrix 72 is also connected to a high input impedance potential measurement device, preferably an electrometer (EM) 76, preferably Model 5113, available from EG&G Instruments, Princeton, N.J. 08543. The inputs to the electrometer 76 from the test cells 40–42 are analog signals at the millivolt level and its output is an analog signal at the volt level. The electrometer includes an amplifier-voltage follower having a high input impedance so that it does not perturb the test cell potential during the measurement. The starting parameters of the electrometer are set by digital data from PC 25.

It is an important feature of the system 10 that the tests of impedance be conducted over a selected range of frequencies and not at only one fixed frequency. Preferably the range of frequencies is 10 Hz to 10,000 Hz. Preferably that range is scanned over a time period from 0.1 second to 10 seconds and a most preferred range of about 0.5 to 2 seconds. The scanning is preferably a step function, i.e., a few milliseconds at each frequency. It has been found that the impedances of the liquids flowing through the hair sample are different at different frequencies.

An important way to detect and characterize charged molecules involves measurement of their impedance behavior over a range of frequencies. In an imaginary three dimensional Cartesian coordinate system, the X axis is time, the y axis is impedance, and the Z axis is frequency. If a scan (over time) only measures impedance at one frequency, it would miss an additional dimension of detection. In effect, each molecule has a "fingerprint" in the three-dimensional analysis (time, impedance and frequency) which can distinguish it from different, but related, molecules. For example, a low molecular weight cationic surfactant may be distinguished from a higher molecular weight cationic polymer in this manner.

This additional dimension of detection can also allow the operator to deconvolute complex situations where multiple molecular species are influencing cell impedance simultaneously.

The analyzer device 75 provides the selected range of frequencies as a sine wave or other AC signal. For example, a sine wave train of signals is placed across the two electrodes of each test cell. The impedance analyzer 75 measures the impedance between those electrodes, at each selected frequency and converts that analog measurement to digital data using its internal A/D converter. The measurement is expressed in umhos in which mhos=1/impedance in ohms and mhos is one million umhos.

The potential measurements from electrometer 76, as analog data, are communicated over line 77 to the input/outboard board 23, which includes a high-speed A/D converter. It uses a 16-bit A/D which operates at preferably 200,000–1,000,000 data points per second, and most preferably about 500,000 data points a second. Such high speed data acquisition enables the system 10 to detect and track the double layer relaxation effect of the sample under test. The input/output board 23 converts the analog signals to digital data which it transmits over line 26 to the PC 25.

Preferably an additional conductivity measurement is made of the liquid flowing in tube 51 to measure the conductivity of the liquids after they have passed through each sample under test. A pair of porous electrodes set at a fixed spacing in an insulative housing 80 is connected to conductivity meter 81 by lines 82,83. The meter 81 is connected to PC 25 by line 84.

Preferably the conductivity meter 99 is used to measure the conductivity of each liquid before it is flowed through a test cell. This provides a basis for comparison of the conductivity of the liquid before it flows through each test cell with the conductivity of the liquid after each test cell.

Preferably the optical refractive index of the flowing stream of liquid is measured after each liquid has passed through each sample under test. Such refractivity measurements provide information, for example, concerning loss of non-colored, non-charged materials of interest (i.e., panthenol) during rinsing. The refractive index detector 90 preferably focuses an infra-red beam across the flow cell, detects changes in the bending of the beam through the liquid using a photodiode or phototransistor as its detector, and produces an analog signal over lines 91,91A to refractivity meter 92. The meter 92 has an A/D converter and outputs digital data to PC 25 representing the refractive index. A suitable refractive index detector and meter is available from Beckman Instruments.

A color meter 95 is positioned in tube 53 to measure the color of the liquids which have passed through the test cells. The color of the liquids in reservoirs 11–14 would be known and may be compared with their colors after having passed through the hair samples. A suitable color meter would focus a beam of white light through the liquid and using a different color filter for each one of three detectors (phototransistor or photodiode), i.e., blue, green and red filters, determine the output. The outputs relate to the color of the liquid. A suitable color meter is the Probe Colorimeter, available from Brinkmann Instruments Co.

The test cells 40–42 may develop changes in the liquid flow (permeability) through each cell. For example, a hair sample in a cell may become compressed or it may become coated with a shampoo or conditioning agent which would add to its restriction to liquid flow through its cell. In order to test such changes in permeability, a first pressure sensor 101 is positioned in tube 35 (before the test cells 40–42) to measure the pressure of the liquid. A suitable pressure sensor (pressure transducer) is Model 205-2 available from Setra (Acton, Mass. 1720). The pressure sensors 100 and 101 transmit analog signals to converter board 23 which converts those signals to digital data and transmits such digital data to PC 25. That digital data may be plotted by PC 25 and printed, as hard copy, by a printer, or displayed on a computer monitor. The PC 25 also controls the timing of the measurements made by the pressure sensors 100 and 101.

The PC 25 is programmed to recognize out-of-limit parameters and to warn the operator that the system needs attention and that the data being collected is likely to be flawed. This type of warning is preferably given by a flashing notice on a screen of a monitor connected to PC 25 and/or an audio signal, such as a buzzer. The out-of-limit parameters are based on data from previous experiments, i.e., by what may be expected to be a normal range. For example, if conductivity of the control ($0.5 \times 10^{-4}$M KCl) is normally about 5 umhos (normally in the range of 4–6 umhos) then the out-of-parameter (abnormal) is set at 5 umhos ±20%. If the impedance is below 4 umhos or above 6 umhos, a warning is given to the operator and a portion of the recording is marked with a suitable label, such as "conductivity control out of limits".

Similarly, a normal range is set, based on experience, for each liquid and for each meter, i.e., a normal range of permeability, conductivity, streaming potential, color and refractive index for the control liquid (reservoir 11) as well as for each test liquid. Any data outside of those normal ranges sets off the corresponding warning alarm which is recorded along with the abnormal data.

If only one test cell were to be used, it would be necessary to test each hair sample by removing the first sample, cleaning the apparatus, and placing the second sample in the test cell. Each test may take a number of hours and it takes additional time to remove each sample, clean and flush the apparatus, and place a new sample in the test cell. By that time the conditions, such as room temperature, etc., may have changed, so that the second test would not exactly replicate the first test. The use of two or three test cells permits more rapid testing so that the same conditions may be maintained.

Using prior art "Paar-KI-EKA" from Brookhaven Instruments an operator would have to change plugs between test solutions, or otherwise intervene in an experiment, providing significant opportunity for error or variance. The present system and method provide computer control over an entire experiment, or set of experiments, without operator intervention.

In the present invention, the important conditions, in practical effect, are held constant so that the experiments may be precisely replicated. One important condition is the pressure of the liquids, and such pressure is precisely maintained within 2% of a standard, under computer control.

The computer monitors the experiments against a set of limits which define out-of-limit parameters (acceptable ranges). It immediately warns the operator if any of the parameters become out of the limits. The limits are based on experimental data. In this way the operator may spot, and correct, problems before invalid data is collected. The parameters which are monitored, and which are recorded in computer memory (instrument log file) include conductivity, flow, and pressure. In addition, the computer monitor, and/or printer, displays those parameters in real time and shows the limits so that the operator may see how close the parameters are to the range limits. This presents, to the operator, real-time graphical information regarding key data and selected instrument parameters including streaming potential, conductivity and flow rate. The parameters (conductivity, flow, pressure, etc.) are recorded, in computer memory, in an instrument log file.

The use of a plurality of permit duplicate plugs to arable, permit duplicate plugs to be tested in sequence using the same liquids and test conditions. For example, a single automated experiment may simultaneously test normal hair, dry hair and damaged hair using the same solutions and test conditions. This permits an immediate and complete characterization of a product, such as a shampoo on three types of hair in a single experiment, to provide additional confidence in its results, if the experiment is replicated, or to find the cause of error, if the experiment is not replicated.

The system uses optical relays to avoid error-causing ground loops and system noise. Preferably all the 110-volt devices, such as the water system, magnetic stirrers, etc., are controlled through the use of optical relays. The computer software allows for the precise timing of treatment and baseline cycles, as well as complete control of liquid pressure, direction of flow (forward or backward flow through the plug) and the repetition of experimental cycles.

Preferably the computer is programmed to flush the system with the test solution as part of an automated clean-up routine to prevent contamination of future experiments by residues of solutions from prior experiments.

The test solution reservoir, under computer control, may be automatically filled from a source of ultra-pure water. The computer will receive information on the pH and conductivity of the test solution and may control the operation of automatic burets to dispense standard salt and buffer materials, into the test solution, until it attains specified pH and conductivity levels. This permits automatic and unattended operation, for example, at night or over a weekend.

The computer software allows for flexibility in the experiments so that they may simulate actual conditions. For example, a shampoo may be flowed through a hair plug, over a few days, continuously or in a sequence, to simulate the build-up of surfactants on the hair due to repeated shampoo treatments.

The system includes a fast electrometer which, through high-speed acquisition, is able to measure rapid changes in electrical effects at the plugs, for example, it may follow double-layer relaxation effects and thereby resolve double-layer effects. A sensor measures the refractive index of the fluid which has been flowed through the sample plugs to characterize the behavior of uncharged materials on the sample.

The computer control of the system, including instrument functions and data acquisition, permits its unattended operation, for example, at night and weekends. The clean-up is also preferably automated, under computer control, and the clean-up may occur at night, so that new experimental runs may be started each morning without a manual clean-up.

The preferred computer software program (Windows 3.1™ on "LabView"™ platform) permits the operator to (i) select a standardized protocol (tests, solutions, cycles, conditions, etc.) from a menu of pre-programmed protocols, or (ii) define a customized experimental protocol using intuitive icons, and the entry of parameters using pop-up menus. The user interacts with the system using the computer software which provides a graphic interface, on the computer monitor, so that the user may use a mouse or keyboard to select the instrument icons, the cycle timing and other conditions. The "LabView" software permits the data produced during the experiments to be entered, via Dynamic Data Exchange (DDE) directly into an analysis spreadsheet such as Microsoft Excel™, Lotus 123™, Quatro Pro™ or other spreadsheet programs. Once the data is incorporated into a suitable spreadsheet program, the user may readily produce reports and graphs regarding the experiments.

I claim:

1. A system for the simultaneous measurement of dynamic streaming potential, dynamic impedance and dynamic permeability by the flow of a liquid through a sample, the system including:

(a) at least two test cells each adapted to removably hold a sample, each test cell having inlet and outlet orifices and a body portion adapted to permit the flow of the liquid from the inlet orifice through the body portion to the outlet orifice;

(b) at least first and second air-tight liquid reservoir means, the first reservoir means to supply a first liquid which is a test solution to provide a set of baseline measurements and the second reservoir means to supply a second liquid whose effect on a sample is to be tested;

(c) pressurized air means connected to the first and second reservoir means to apply constant air pressure, within two percent of a selected air pressure, to the liquids therein;

(d) a valve matrix and a series of liquid flow lines leading from the first and second reservoir means to the valve matrix and from the valve matrix to the input orifices;

(e) a programmable electronic computer system means to provide a program of electric control signals to operate the valve matrix and thereby control the flow of liquid from one of the reservoir means through a selected test cell;

(f) a pair of porous electrodes within each test cell adapted to be positioned at opposite ends of the sample therein;

(g) an electrical switch matrix and a electrometer electrically connected to each pair of electrodes through the switch matrix and connected to the computer means, the electrometer measuring the electrical potential across the pair of electrodes when liquid flows therethrough;

(h) impedance measurement means connected to the computer means and to the switch matrix and connectable through the switch matrix to the electrodes, the impedance measurement means to generate and apply to the electrodes signals a plurality of different frequencies over a selected range of frequencies and to test impedances of a sample in the test cell at the selected different frequencies; wherein (i) the valve matrix comprises a set of operable valves in the liquid flow lines, the valves being electrically connected to, and controlled by, the computer system means and the switch matrix comprises a set of switches electrically connected to, and controlled by, the computer system means; and (j) program means to program the computer system means to operate the computer system means in a dynamic mode in which in each test cell, in sequence, a first liquid test solution is flowed through the test cell and then, without removal of a sample from the test cell, a second liquid is flowed through the same test cell.

2. A system as in claim 1 wherein the frequencies are in the range of 10 Hz to 10,000 Hz.

3. A system as in claim 1 and further including a wide bandwidth low noise mercury wetted switch means to switch the electrodes between the electrometer and the impedance measurement means, said switch means being controlled by said computer means.

4. A system as in claim 1 wherein said electrometer has an analog output and said system includes an analog-to-digital converter.

5. A system as in claim 1 and further including a liquid flow meter connected to said output orifices to measure the flow therefrom, said liquid flow meter being connected to said computer means.

6. A system as in claim 1 and further including a first liquid pressure sensor and a second liquid pressure sensor, both connected to the said computer means, the first pressure sensor positioned to measure the pressure of liquid flowing into the test cells and the second pressure meter positioned to measure the pressure of liquid flowing out of the test cells.

7. A system as in claim 1 and further including first and second conductivity meter means to measure the conductivity of liquid flow, the first conductivity meter means positioned to measure the conductivity of the liquid before it enters the test cell and the second conductivity meter means positioned to measure the conductivity of the liquid as it exits the test cell.

8. A system as in claim 1 and further including a third air-tight liquid reservoir connected to the liquid flow lines and the source of air pressure and adapted to contain a liquid whose effect on the sample is to be tested.

9. A system as in claim 1 wherein said system further includes a first conductivity meter means connected between the reservoirs and the test cells to measure the conductivity of liquids flowing from a reservoir to a test cell and a second conductivity meter means connected in series with the test cell outlet orifices to measure liquid after it has flowed through a test cell, each conductivity meter being connected to the computer means.

10. A system as in claim 1 wherein the switch matrix includes a set of mercury wetted switches.

11. A system as in claim 1 and further including a refractive index meter means to measure the refractive index of a liquid after it has flowed through one of the samples.

12. A system as in claim 11 and further including a third and a fourth air-tight liquid reservoir connected to the liquid flow lines and the source of air pressure, the third and fourth reservoirs adapted to contain liquids whose effect on the sample is to be tested.

13. A method for the measurement of streaming potential and conductivity by the flow of a liquid through at least two separate samples, the method including the steps of:

(a) placing each sample in a separate test cell, each test cell having input and output orifices and a body portion adapted to permit a flow of liquid from the input orifice through the cell body portion to the output orifice;

(b) generating a program of electric control signals from a programmable computer system to control the timing, switching, data acquisition and the flow of liquid through each test cell;

(c) flowing liquids through each test cell, from at least the first and second air-tight liquid reservoirs, the first reservoir containing a first liquid which is a test solution to provide a set of baseline measurements and the second reservoir containing a second liquid whose effect on the samples is to be tested;

(d) applying pressurized air, which is constant within two percent of a selected pressure, to the first and second reservoirs to apply pressure to the liquids therein;

(e) measuring the electrical impedances over a selected range of frequencies by applying signals of the frequencies across a pair of electrodes within each test cell and using an impedance analyzer connected to the electrodes and to the computer system for the impedance measurement, the electrodes being positioned at opposite ends of a sample therein;

(f) using an electrometer electrically connected to the electrodes and the computer system to provide a streaming potential measurement; and (g) operating the computer means in a dynamic mode to control a set of electrical operable valves in which the first liquid test solution is flowed through each test cell and then, without removal of a sample from the test cell, the second liquid is flowed through the same test cell.

14. A method as in claim 13 wherein the liquids are flowed through a first test cell from the reservoirs in a selected sequence and thereafter liquids are flowed through a second test cell from the same reservoirs in the same sequence.

15. A method as in claim 13 and including measuring the conductivity of each liquid both before and after each liquid flows through the test cells using two conductivity meters connected to the computer system.

16. A method as in claim 13 and including measuring the flow rate of each liquid as it exits each test cell using a flow rate meter.

17. A method as in claim 13 and including filling a third air-tight liquid reservoir with a third liquid whose effect on each sample is to be tested and applying air pressure to the third reservoir and flowing the third liquid through each test cell.

18. A method as in claim 13 and generating the signals in the frequency range of 10 Hz to 10,000 Hz.

* * * * *